United States Patent [19]

Eaton et al.

[11] Patent Number: 4,475,035

[45] Date of Patent: Oct. 2, 1984

[54] METHOD AND APPARATUS FOR SCANNING

[75] Inventors: Homer L. Eaton; John D. Shaylor-Billings, both of Leucadia, Calif.

[73] Assignee: Vektronics, Inc., Carlsbad, Calif.

[21] Appl. No.: 383,950

[22] Filed: Jun. 1, 1982

Related U.S. Application Data

[63] Continuation-in-part of Ser. No. 272,757, Jun. 11, 1981, abandoned.

[51] Int. Cl.³ ............................................... H01J 3/14
[52] U.S. Cl. ..................................... 250/236; 250/572
[58] Field of Search ............... 250/562, 563, 236, 235, 250/572, 216, 234, 560; 358/106, 205, 206; 350/6.4, 6.5; 356/445

[56] References Cited

U.S. PATENT DOCUMENTS

| | | | |
|---|---|---|---|
| 4,208,589 | 6/1980 | Dashwood et al. | 250/560 |
| 4,259,013 | 3/1981 | Faxvog et al. | 356/237 |
| 4,348,114 | 9/1982 | Neale et al. | 250/563 X |
| 4,392,120 | 7/1983 | Mita et al. | 250/563 X |

FOREIGN PATENT DOCUMENTS

| | | |
|---|---|---|
| 1170179 | 12/1967 | United Kingdom . |
| 1328877 | 10/1970 | United Kingdom . |
| 1405331 | 1/1973 | United Kingdom . |

*Primary Examiner*—David C. Nelms
*Attorney, Agent, or Firm*—Gausewitz, Carr, Rothenberg & Edwards

[57] ABSTRACT

The surface of a part to be identified or inspected is scanned by a laser beam projected normal to the surface to be scanned from the end of a rotating arm in a circular scan pattern. A small collector lens is fixed to the end of the rotating arm and has a hole through which the projected beam passes. The part moves across the scan pattern in a direction perpendicular to the projected beam, and intensity of reflected light received by the lens and transmitted to a detector provides precision information concerning surface characteristics, orientation and discontinuities.

12 Claims, 9 Drawing Figures

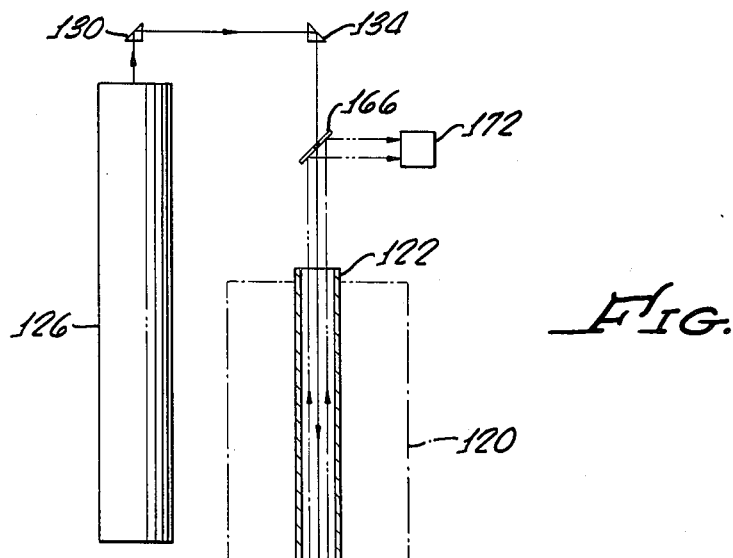
_FIG. 7._
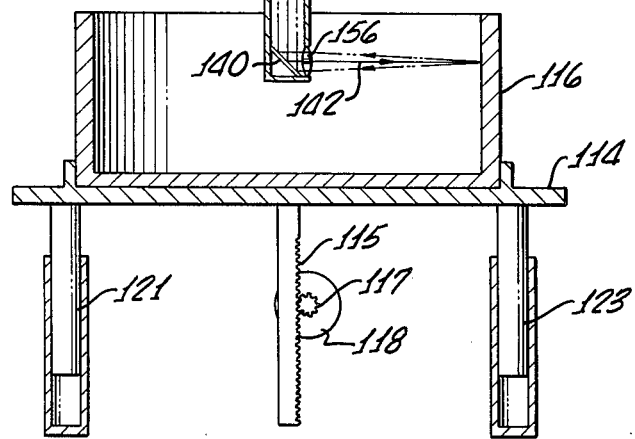
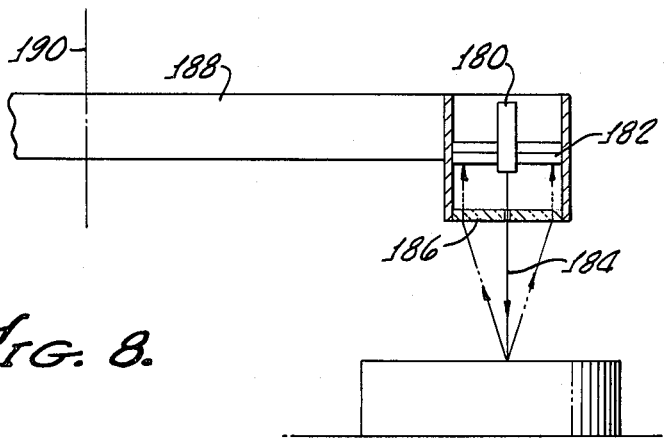
_FIG. 8._

METHOD AND APPARATUS FOR SCANNING

This is a continuation-in-part application of Ser. No. 272,757, filed June 11, 1981 now abandoned.

BACKGROUND OF THE INVENTION

The present invention relates to surface scanning of parts and more particularly concerns improved scanning methods and apparatus to provide precision information concerning surface characteristics, configuration, orientation and discontinuities.

Electro-optical parts inspection and identification broadly involves the collection and analysis of light reflected from the surface of an object being monitored. In general, prior scanning apparatus, such as the video camera, for example, involve the equivalent of a point source of scanning. Light is transmitted to and received from the part at varying angles for different points of the object being scanned. Such arrangements require fixed positioning and orientation of the part being scanned so that the part is usually mounted in a fixture that predetermines position and orientation with respect to the scanning device. A point scanning source, such as that providing a conical scan, for example, has an illuminating beam that strikes different portions of the scanned surface at different angles. Surface elevation characteristics, such as cavities or protuberances, will reflect differently in different orientations and different angles of illumination so that reflection intensities afford less useful information.

For optimum precision in identification and measurement of surface detail, for improved repeatability of measurement, and for greater freedom from orientation and position restraint, all points on the surface of the part should be illuminated by light beams that are at all times parallel to one another, or always normal to a selected plane through the part. For example, such an orthogonally directed scan is required for measurement of part dimensions in a plane normal to the beam and for measuring surface elevation features in directions parallel to the beam. With such a perpendicular pattern of parallel scanning beams there is available a considerably greater flexibility in part position and orientation relative to the scanner, and reflections from surface areas of unique roughness configurations will have greater uniformity and repeatability. The lack of orthogonal scanning imposes substantial limitations on usefulness of the scanning.

In those prior art scanning devices employing a projected scanning beam and a receiver for collecting light reflected from the object, the receiver must be large enough to receive light reflected from all areas of the object that are illuminated during the entire scan. In such arrangements the size of the part that can be scanned is relatively small, being limited by practical and economic considerations that limit the size of a light receiver, such as an optical lens, a collecting mirror or an array of detectors or optical fibers.

Accordingly, it is an object of the present invention to provide scanning apparatus and methods that avoid or minimize above-mentioned problems.

SUMMARY OF THE INVENTION

In carrying out principles of the invention in accordance with a preferred embodiment thereof, a rotatably mounted scanner beam support includes means for projecting an energy beam for rotation with the support about the support axis. Receiver means are mounted adjacent the projected energy beam for rotation therewith to receive beam energy reflected from an object upon which the beam impinges. In a specific embodiment, a light beam is projected from a rotating mirror in parallel directions normal to the surface of an object being scanned. The beam is projected through a small collecting lens coaxial with the light beam and mounted for rotation with the projected beam, the lens collecting reflected light for transmission to a detector.

A method according to the present invention includes moving a projected energy beam in a scan pattern, collecting reflected energy in a narrow area extending along the scan pattern, relatively moving the object and scan pattern, and indicating intensity of reflected energy collected at the area. The beam may be projected parallel to an axis of rotation to provide a cylindrical scan pattern, or it may be projected perpendicular to the axis of rotation to provide a planar scan pattern for scanning the interior surface of a cylindrical object within which the scanner is positioned. Methods and apparatus of the invention provide a true two-dimensional or orthographic view.

BRIEF DESCRIPTION OF THE DRAWINGS

FIG. 7 illustrates a modified form of the apparatus of the invention;

FIG. 8 illustrates a modification in which the laser, detector and collecting lens are rotated together.

DETAILED DESCRIPTION

Figure 1:
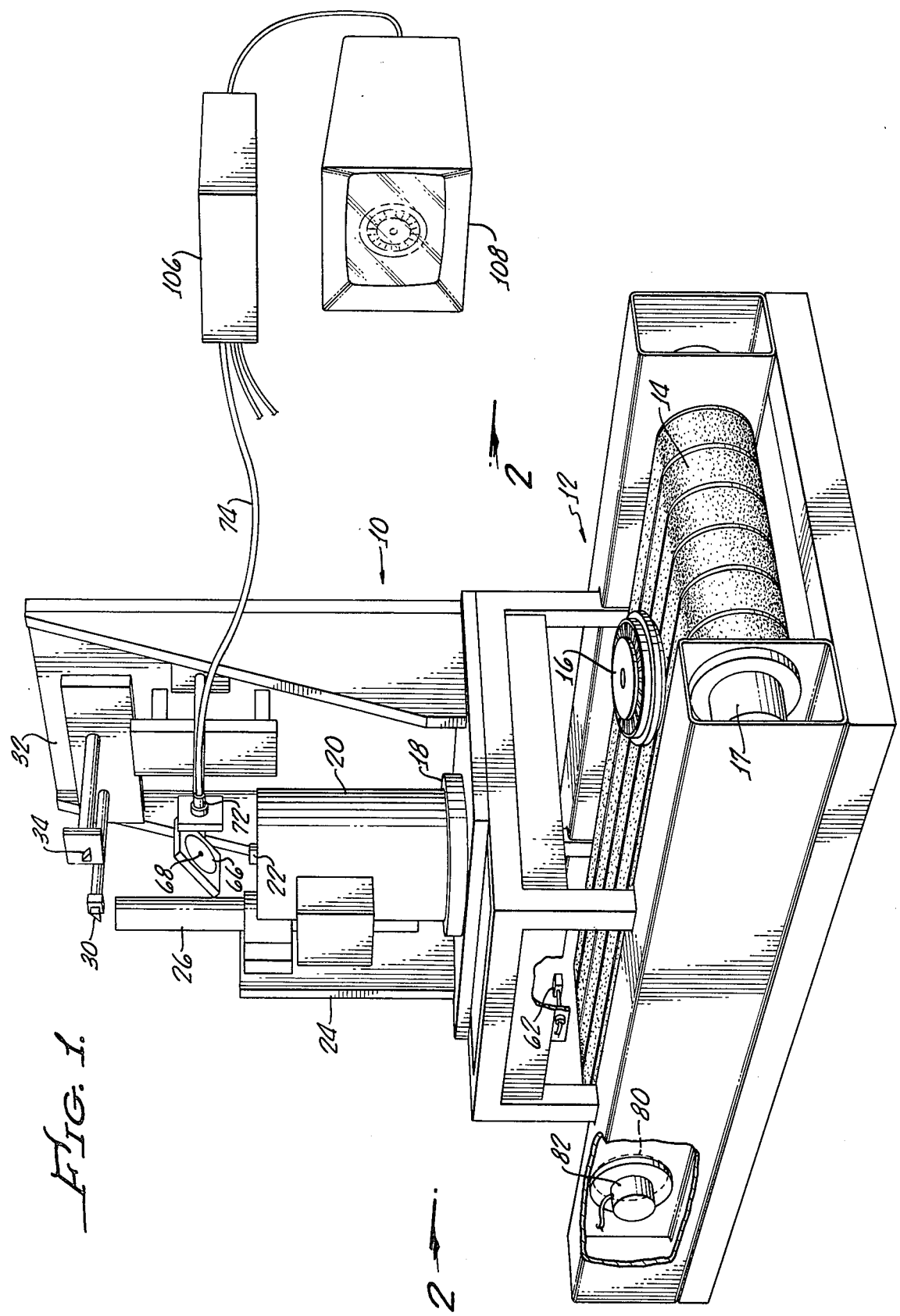
FIG. 1 is a pictorial illustration of scanning apparatus embodying principles of the present invention.

As illustrated in FIG. 1, a scanner embodying principles of the present invention comprises a support structure 10 fixedly supported above and adjacent to a conveyor 12 having a movable belt 14 on which is placed an object 16 that is to be scanned. The object to be scanned can be of many different sizes, shapes and construction, being generally illustrated as a transmission stator. The conveyor is driven by a motor 17 to move the belt and the object from the left to right as viewed in FIG. 1, close to and directly beneath the scanning apparatus, and entirely across the scan pattern thereof.

The support structure comprises a rigid base 18 on which is fixedly mounted a motor 20 having a hollow vertical shaft 22 that is rotated at high speed by the motor. Fixedly mounted to an upstanding sidewall 24 is an energy beam generator in the form of a laser 26 that generates and projects a very small cross-sectional area light beam 28 to a first 90° reflecting prism 30 mounted at the upper end of an upstanding rear wall 32 of structure 10. Prism 30 turns the light beam through 90° to a second 90° reflecting prism 34, also fixed to the upper end of wall 32, and positioned in alignment with the center of the hollow motor shaft, whereby the beam is reflected downwardly through the center of the shaft 22. At the bottom of the shaft is mounted a third 90° reflecting prism 40 (FIG. 3) which again turns the light beam at an angle of 90° so that the beam is now directed perpendicular to the axis of rotation of the motor shaft.

The scanner support structure includes an enlarged lower section 42 of generally inverted dish-shaped configuration having a downwardly facing end closed and sealed by a high strength rigid protective plate 44. Plate 44 is preferably made of a completely transparent material but may be made of any suitable opaque material provided that a transparent annular area 46 completely circumscribing the lower section 42 of the support structure is formed in the bottom plate.

Fixedly connected to the end of the hollow motor shaft 22 is a rotatable arm in the form of a disc 48 in the radially outer end of which is mounted a fourth 90° reflecting prism 50, positioned to receive the light beam from prism 40 and turn it through 90° along the path indicated by reference character 52. Accordingly, as the motor shaft is rotated, prisms 40 and 50 and disc 48 rotate about the shaft axis, causing the projected laser beam 52 to scan in a right circular cylindrical pattern centered on the axis of rotation of the scanner and having a radius equal to the radial displacement of the reflective prism 50 from the shaft axis. The arrangement provides an orthogonal scan, with the scanning beam always exiting parallel to the rotation axis and normal to the part supporting surface of conveyor belt 14.

A lens 56 having an axial hole 58 extending completely therethrough is fixedly mounted in a support 60 that is fixed to the end of rotating disc 48. The lens and its hole are coaxial with the projected beam 52 which passes freely through the lens. The lens is focused on the point of impingement of the beam upon the object being scanned.

A reference generator in the form of a light sensitive diode or equivalent 62 is fixed to the bottom of plate 44 in the path of the projected beam 52 so as to be illuminated momentarily by the beam during each cycle of its rotation.

Light projected from the rotating energy beam 52 is reflected from a very small area of the object upon which the beam impinges and some of this reflected light is collected by the lens 56 which collimates the collected light and transmits it back to the reflecting prism 50. The collimated retroreflected light is then retro-directed along several legs of the outgoing laser beam path, from the prism 50 back to prism 40 and then upwardly along and through the hollow motor shaft. However, between the upper end of the motor shaft and the reflecting prism 34 there is mounted a 90° turning mirror 66 that has a central aperture 68 through which the outgoing laser beam passes without disturbance. The small hole 68 in the reflector 66 does not significantly affect the reflection by this mirror of the received collimated reflected energy which is directed to a detector 72 that provides an output signal on lead 74 having a magnitude directly related to the intensity of the light received thereby.

The belt 14 of conveyor 12 is entrained over a second roller 80 at the end opposite the motor and a conveyor position detector 82, such as a conventional incremental shaft encoder, is mounted to the roller so as to provide from the detector encoder 82 a series of pulses each of which denotes an increment of rotation of the roller and thus an increment of motion of the conveyor belt 14.

Figures 4, 5, 6:
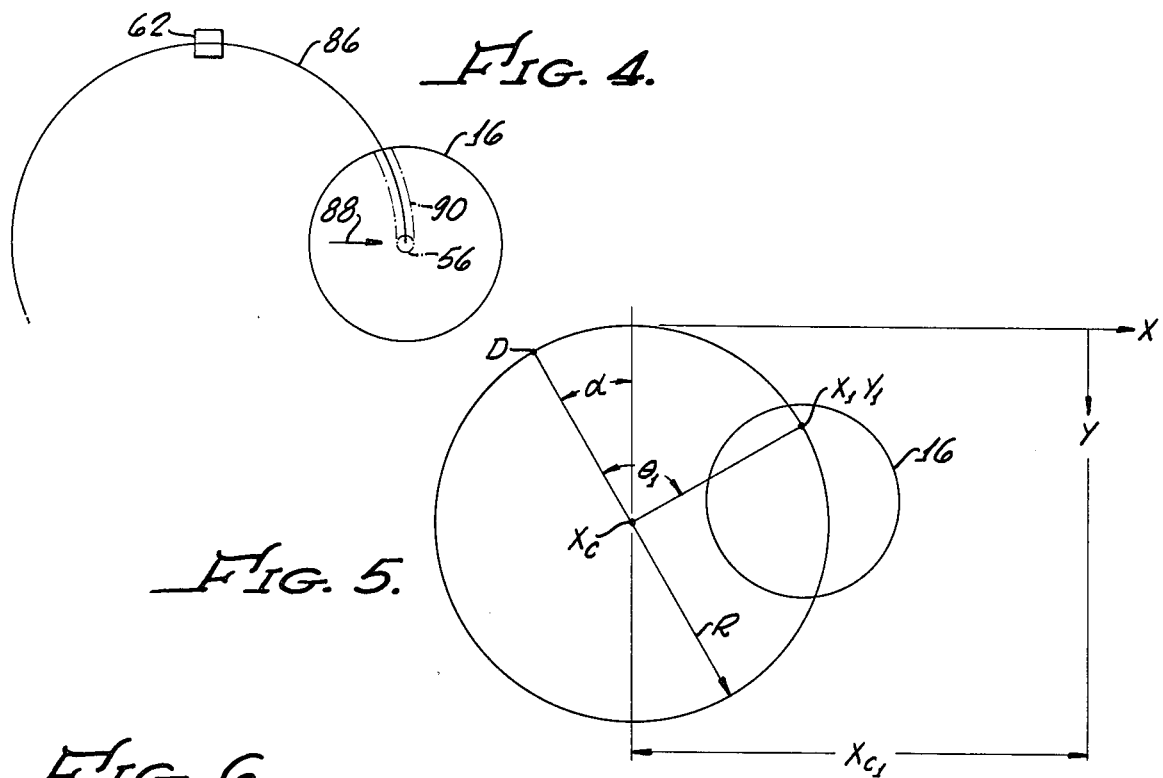
FIG. 4 diagrammatically depicts the circular scan pattern that moves repetitively across the object being monitored.
FIG. 5 illustrates geometry that defines coordinates of the circular scan.
FIG. 6 is a block diagram of electronic components used to generate signals defining beam intensity at different points in the circular scan axis.

As can be seen in FIG. 4, the laser beam moves in a cylindrical scan pattern and scans a circular path 86 that crosses the part 16 as the latter moves relative to the scan path 86 in the direction indicated by arrow 88. The receiving lens 56 also moves in a circular path and collects light over a narrow annular area 90 which is in effect the scanning path of the light receiving lens. Thus, the lens scans the moving part 16 in a circular path to receive light reflected from an annular area at or aligned with the circular scan path 86 of the light beam. As the part 16 moves across the scan path 86, the beam makes many passes across the part. With the relative dimensions of scan and part as illustrated in FIG. 4, such dimensions being merely exemplary, the part is initially scanned repetitively by the left-hand side (as viewed in FIG. 4) of the scan path and then it is scanned repetitively by the right-hand side of the scan pattern.

From the pulse trains provided at the outputs of reference detector 62 and conveyor position encoder 82, the position of the area of the part illuminated by the beam at each of a large number of points in its scan is determined. Geometry and equations for identifying beam position are basically the same as those described in the Profile Scanning Apparatus of U.S. Pat. No. 4,122,525, differing primarily in that instead of reading out position coordinates solely on intersection of the beam with a part boundary, a clock is employed to read out signals identifying position coordinates at selected fixed time intervals.

Geometry of the point position identification is illustrated in FIG. 5. Part 16 travels, together with a moving coordinate system XY, relative to the laser scan of radius R. Detector 62 provides a reference at point D, which lies on a radius at an angle $\alpha$ with respect to the Y axis. The position of any point on the beam scan at an angle $\theta_1$ with respect to the scan radius through the reference point is identified by the coordinates $x_1$, $y_1$, in the moving coordinate system defined by the following equations:

$$x_1 = X_c - R \sin(\theta_1 - \alpha) \qquad \text{Eq. (1)}$$

$$y_1 = R - R \cos(\theta_1 - \alpha) \qquad \text{Eq. (2)}$$

where $X_c$ is the X coordinate of the scan center.

Measurements are based upon pulses produced by a fixed repetition rate pulse generator so that $\alpha = K_1 \times K_2$ where $K_1$ is the number of such pulses that occur in the time required for the beam to travel through the reference angle $\alpha$, and $K_2$ is the angular distance through which the beam travels along the scan pattern in the interval between two successive pulses. Accordingly, equations (1) and (2) become $$x_1 = X_c - R \sin[(N_1 - K_1)K_2] \qquad \text{Eq. (3)}$$

$$y_1 = R[1 - \cos(N_1 - K_1)K_2] \qquad \text{Eq. (4)}$$

in which $N_1$ is the number of pulses occurring in the time required for the beam to travel from the reference point D to the point $x_1 y_1$. Thus, equations (3) and (4) define the coordinates of points in the beam scan in terms of fixed quantities R, $K_1$ and $K_2$ and variable quantities $X_c$ and $N_1 X_1$. $X_c$ is the quantity obtained from the incremental encoder 82 that signals position of the conveyor and $N_1$ is determined by count of pulses of the pulse train to a given point.

Illustrated in FIG. 6 is an electronic circuit that will generate signals defining beam intensity and coordinates at selected clock intervals. Beam reference sensor 62 generates pulses that are sent to reset a counter 92 having a counting input on line 94 from a system clock 96. Each count of the counter is clocked into and stored in storage register 98 which, accordingly, provides outputs respectively representing successive clocked angular positions of the beam in its rotating scan. The output of conveyor position detector 82 is fed to a second counter 100 of which the outputs are fed to a storage register 102 at intervals determined by the timing pulses from clock 96. Thus, register 102 stores signals representing successive positions of the conveyor and thus, successive positions of the part, in the direction of conveyor travel at successive clock periods. The output I of the reflection detector 72 is fed through a gate 104 under control of the system clock 96 and all the signals are fed to a data processor 106 (FIG. 1). The signals from storage 98 and 102 and from the reflection detector 72, which, of course, may be stored and used for manual computation and plotting of reflected energy intensity at different coordinate positions, are preferably handled by digital computation. Details of the computation and data processing form no part of this invention. The analog reflection intensity signals may be digitized and stored together with position coordinate information and then compared to similar stored intensity and position signals that have been previously generated on a scan of a part of a known configuration. The comparison will indicate the correspondence of the newly scanned part with the reference part. Alternatively, or, in addition, the stored information representing intensity and coordinate position may be fed to an oscilloscope 108 to provide a visual display of the scanned object. Accordingly, it will be seen that the signals generated by the reflected light intensity detector 72, the beam reference sensor 62 and the conveyor position detector 82 collectively define intensity of light reflected from a number of points on the object and also define the relative positions of such points, therefore enabling a plot of intensity over the area of the object to be made. This information is readily available from the output reflected beam intensity, the output $N_1$ indicating radial angle of the beam (position of the beam in its circular scan) and the linear displacement $X_c$ relative to the reference system (the conveyor system). This is done for a large number of points as the part is moved through the cylindrical beam scan.

In an exemplary embodiment the disc rotates at 1800 revolutions per minute, and the conveyor travels at 1.25 inches per second, so that the part advances approximately 0.042 inches during each beam rotation. However, as mentioned previously, the part is scanned twice, by the left segment of the circular beam as the part enters the scan, and by the right segment of the beam scan pattern as the part leaves the scan, thus improving the resolution.

It will be readily appreciated that many modifications may be made in the apparatus employed to provide this orthogonal scanning. For example, as illustrated in FIG. 7, with minor modification the principles of the present invention may be employed to scan the interior of a cylindrical part, such as the interior surface of a brake drum 116. In this arrangement, the laser 126 directs its narrow beam through the hollow shaft 122 of a motor 120 via a pair of 90° turning prisms 130, 134 and through the aperture of a turning mirror 166. Light passing through the shaft 122 is reflected by a third turning mirror or prism 140 at the bottom of the hollow shaft, this prism, in this embodiment, being the final prism from which the rotating and scanning beam 142 is projected. The beam is projected in a direction perpendicular to the axis of rotation and perpendicular to the interior surface of the part 116 that is being scanned, thereby scanning a circular path around the interior of the drum in a plane that is always normal to the drum surface and normal to the axis of rotation. In effect, the beam 142 scans along successive radii of a circle lying in a plane normal to the brake drum surface and normal to the rotational axis. Light reflected from the drum surface is received by a collector lens 156 having an aperture therethrough through which the outgoing beam 142 passes without disturbance. Lens 156 is fixedly mounted to the shaft 122 to rotate together with the turning prism 140. Light collected by the lens 156 is retroreflected through the hollow shaft via prism 140 to the mirror 166 from which it is reflected to a light intensity detector 172.

To enable the scanning plane to move relative to the drum surface, the drum 116 is mounted upon a vertically movable table 114 that is driven vertically by a rack and gear 115, 117, and a motor 118 and guided in its motion by means of guides 121, 123. A vertical position encoder and a beam angular reference generator (not shown) are provided to establish position of the beam relative to the drum surface during the scan.

Schematically illustrated in FIG. 8 are portions of still another modification of the scanner of the present invention. In this arrangement a small laser 180, such as a continuous wave laser diode of the GOLS series made by General Optronics of South Plainfield, NJ, is mounted in the center of an array 182 of photo diodes to project a beam 184 through a central aperture of a lens 186. The laser, photo diode array and lens are all mounted at the end of a rotating scanner support arm 188 that itself is mounted for rotation about an axis indicated at 190. Suitable electrical leads (not shown) are carried through the rotating arm for providing power to the laser and transmitting intensity signals from the photo diode array. This arrangement operates just as the previously described arrangements. Light from the laser is transmitted through the hole in the lens to the surface of a part to be identified. Light reflected from the part is collected by the lens and transmitted to the photo diode detector to provide the desired intensity signals. Use of a larger photo diode detector array provides more information by collating reflected light from a larger area. A Fresnel lens 186, aligned with the projected beam and detector, is preferred for the larger detector.

Figure 3:
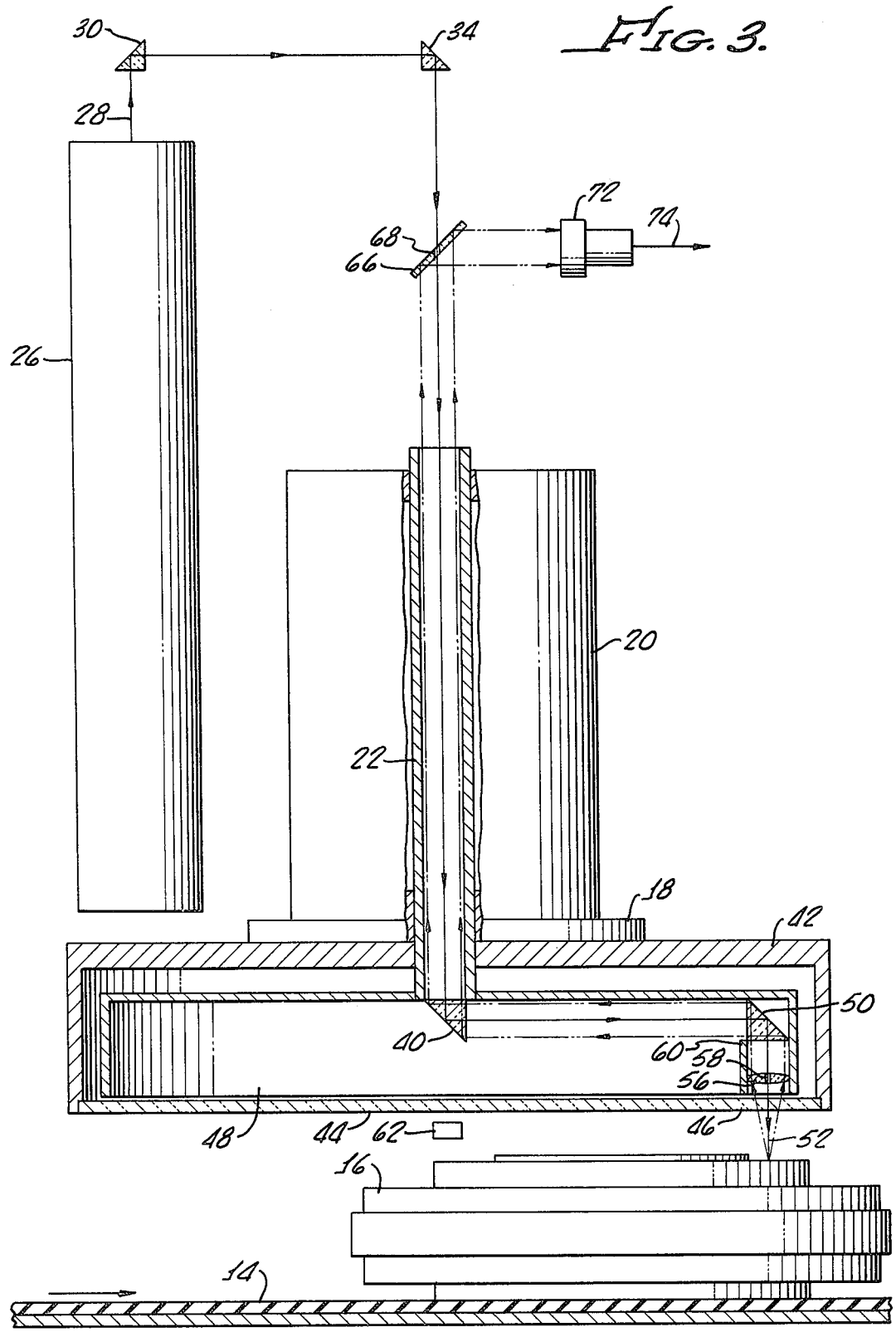
FIG. 3 is a side elevation of the apparatus of FIG. 1.

It can be readily seen, as illustrated in FIGS. 3 and 8, that the axis of the solid-state receiver 188 of FIG. 8 or the equivalent lens 56 of FIG. 3 is coaxial with the laser beam. This arrangement assists in optimum collection of reflected light over an area that is centered upon the common axis of the laser beam and the lens or receiver axis. In the arrangement illustrated in FIG. 8, the receiver or light detector 182 need not be an array of receiving elements but may be a solid light sensitive material having a surface normal to the laser beam axis, with the solid-state laser as in the arrangement of FIG. 8, projecting its beam through a central aperture of the receiver. In such an arrangement, or in the arrangement of FIG. 8 employing an array of photo diodes, the light detector is sufficiently large so that the assembly of laser and receiver may be placed at the end of the rotating arm 188 at a position so close to the object being scanned that no interposed collecting lens 186 need be employed. Alternatively, the solid receiver may be moved to the position of the lens 186 with a laser beam being projected through an aperture of the receiver and coaxial with the receiver axis.

Figure 9:
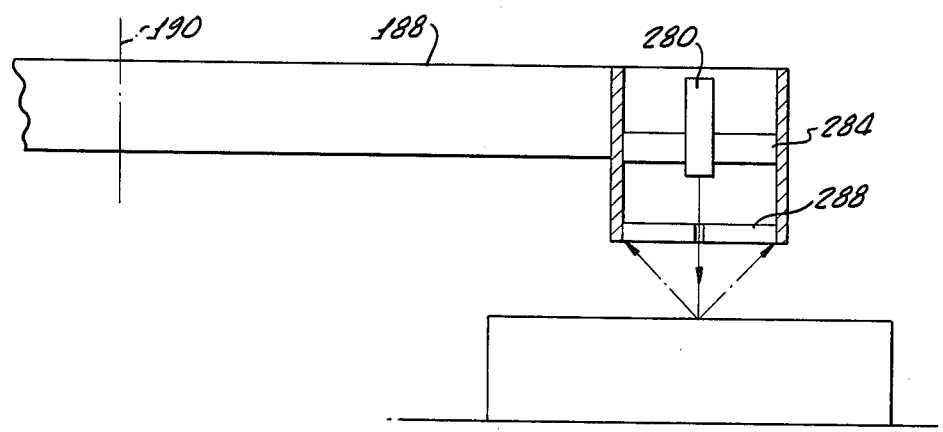
FIG. 9 illustrates a further modification.

FIG. 9 illustrates such laser and receiver assembly wherein a small solid-state laser 280 mounted in a laser support 282 at the end of rotating arm 188 projects a light beam perpendicular to the surface of the object being scanned and through the central aperture of a solid receiver 282 having a receiver axis coaxial with the laser beam axis. The receiver is fixedly mounted on the end of arm 188 in close proximity to the object being scanned. The size of the receiver and its proximity to the scanned object improve operation without an interposed lens.

Figure 2:
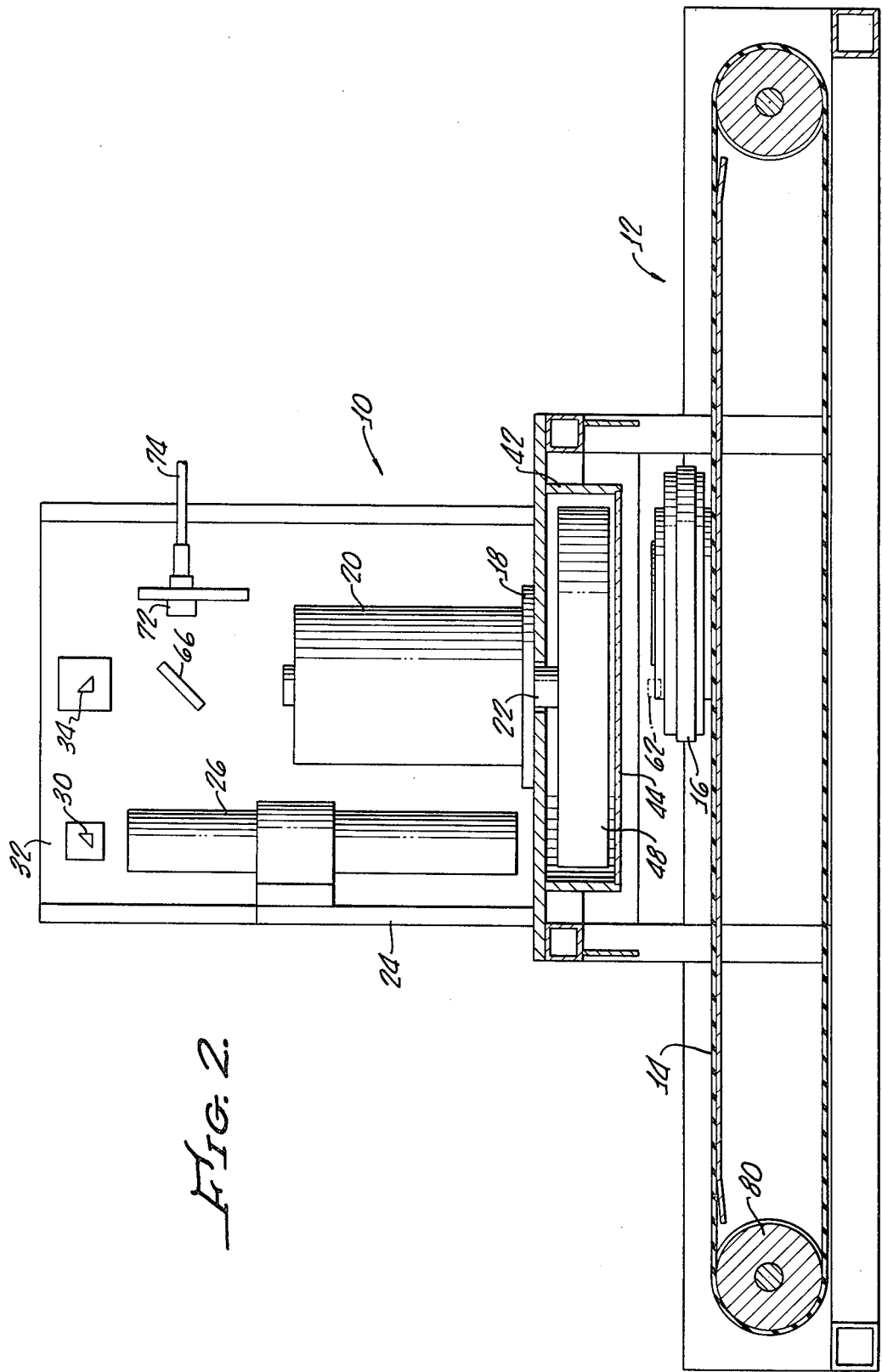
FIG. 2 is a simplified elevational section of the apparatus of FIG. 1.

It is contemplated that the laser 26 of FIGS. 1, 2 and 3 be replaced by a laser distance measuring system, such as, for example, the Laser Measurement System 5501A of Hewlett Packard. This system employs two laser beams of different wave lengths and both interferometry and Doppler techniques to determine distance to a beam reflecting surface that is moving toward or away from the laser beams. Such an arrangement, when employed in the rotating scanner described herein, provides quantitative measurement of surface elevational configuration. For example, assuming the scanning beam, which is moving in its scan pattern along the surface of a part, crosses a part having an elevation change. As the horizontally scanning beam moves to a point on the surface of a greater elevation, it is reflected from a lesser distance from the laser receiver. In effect, distance to the reflecting surface has changed, thus enabling a Doppler measurement of the elevation.

For inspection of surface features of parts of contoured surfaces it is desirable to maintain the orthogonal relation between the energy beam and the surface beam measure. Accordingly, for such application the final turning prism 50 and lens 56 of FIGS. 1, 2 and 3, or equivalent components of other embodiments, are mounted with one or two degrees of pivotal freedom relative to the scanner support arm so that the direction of the projected beam 52 can be automatically changed to maintain the beam perpendicular to the surface of the part. This arrangement employs pivotal mounting of the mirror and lens, and a servo system that senses departure of reflected light from maximum intensity to control the projected beam direction so as to maximize intensity. Such a system more readily detects surface blemishes or discontinuities. Such discontinuities appear as a sharp drop in intensity to the detector, but of a duration short enough to be filtered from the operation of the servo system that controls beam direction so as to maximize beam intensity over a somewhat longer period.

A relatively large solid-state light detector may be arranged with different segmental areas that yield mutually distinct signals in response to received light, so as to give added information. For example, if the portion of the object surface upon which the laser beam impinges is slightly tilted so that maximum intensity of the reflected beam will be angularly shifted from the beam axis, such a segmented receiver will provide information concerning such angular shifting, including the direction in which the intensity maximum is shifted, and thus provide information indicative of both reflectivity and inclination or other characteristics of the surface of the object being scanned. The beam axis may be angularly shifted in a selected search pattern, and those positions yielding greater intensity are noted, remembered and employed to shift the beam axis so as to obtain a beam axis orientation that produces maximum reflection intensity, which is the desired condition of perpendicularity of the beam to the surface being scanned.

Other methods may be employed to maintain the scanning laser beam in a condition of perpendicularity to the surface being scanned. For example, the solid receiver may be formed with a reticular pattern that is established to yield a direction for the sensor to be moved to achieve a decreased angular deviation from the surface normal. Alternatively, a circular distribution of concentric sensor rings will yield a smaller or larger angle sensed, depending upon which of the concentric sensor or receiver circles produce an output signal. This allows the system to sense small changes in the deviation from the surface normal. Thus, selection of a smaller radius of such receiver rings provides a collecting element sensitive to small angles of deviation from surface normal. Conversely, a larger radius yields a broader response to angular deviation.

The foregoing detailed description is to be clearly understood as given by way of illustration and example only, the spirit and scope of this invention being limited solely by the appended claims:

What is claimed is:

1. Apparatus for scanning the surface of an object comprising a support,
    means for mounting the support for rotation about a rotation axis,
    means for rotatably driving the support,
    means carried by the support for projecting an energy beam parallel to said axis is a scan pattern,
    an object carrier mounted adjacent said support for transporting an object to be scanned across said scan pattern, whereby areas on the surface of an object carried by the carrier are successively illuminated by said energy beam,
    position means for generating signals representing position of said carrier relative to said scan pattern and position of the beam in said scan pattern,
    energy receiver means mounted to said support for receiving energy reflected from said object parallel to said axis and for generating intensity signals having a magnitude related to intensity of received energy and
    data means responsive to said receiver means and to said position means for generating signals defining both intensity of energy reflected from said illuminated areas at selected clock intervals and relative coordinates of said illuminated areas at said selected clock intervals.

2. The apparatus of claim 1 wherein said position means comprises a beam reference sensor, and including a carrier position detector, and wherein said data means comprises a system clock, means responsive to said clock and to said reference sensor for storing beam angular positions at said clock intervals, means responsive to said clock and to said carrier position detector for storing carrier positions at said clock intervals, and means responsive to said clock and to said energy receiver means for generating said intensity defining signals at said clock intervals.

3. The apparatus of claim 1 including means responsive to said signals defining intensity and coordinates for generating a visual display of relative intensities of reflected energy over the surface of the scanned object.

4. The apparatus of claim 1 wherein said carrier extends entirely across and beyond both sides of the scan pattern, whereby an object on the carrier is scanned both as it enters the scan pattern and as it leaves the scan pattern.

5. The apparatus of claim 1 wherein said means carried by the support comprises a laser mounted on said support for rotation therewith, and wherein said energy receiver means comprises a light sensitive detector on the support and coaxial with said laser for rotation therewith, said detector having an aperture for passing said light beam.

6. A method of scanning the surface of an object comprising moving a scanning energy beam in a circular pattern across the object to successively illuminate small areas of the surface of the object, relatively moving the object and scan pattern, generating position signals defining position in a plane of a plurality of said illuminated areas at selected clock intervals, moving a scanning receiver across the object in synchronism with the energy beam to receive energy reflected from said illuminated areas back along the path of the energy beam, and generating, from reflected energy received by the receiver, intensity signals having magnitudes directly related to intensities of energy reflected from said illuminated areas at said clock intervals.

7. The method of claim 6 wherein said steps of generating position signals comprises generating beam position signals (N) representing successive angular positions of the beam in its circular scan pattern at said clock intervals, and generating scan pattern position signals ($X_c$) representing relative positions of the scan pattern and object at said clock intervals, whereby said beam position signals and said scan pattern position signals collectively define positions of said illuminated areas at said clock intervals.

8. A method of surface inspection of a part comprising projecting a laser beam in a circular scan pattern of parallel beam paths, moving a part in a direction substantially perpendicular to the beam to cause the beam to impinge upon and to be reflected from many points on the surface of the part, detecting intensity of light reflected from the part surface along the path of the laser beam, generating reflected energy intensity signals having a magnitude directly related to the intensity of light reflected along the path of the laser beam, sampling the reflected energy intensity signals at selected clock intervals, and defining positions of said laser beam at said selected clock intervals in a coordinate system fixed relative to the part.

9. The method of claim 8 including the step of providing a visual display of detected intensities over the area of the part.

10. Surface scanning apparatus comprising a rotatably mounted support, means for rotating the support about an axis, a part carrier for moving a part past said rotatably mounted support, a laser mounted on said support for rotation therewith to project a light beam parallel to said axis to illuminate areas of a part moved by the carrier past said support, and a light sensitive detector mounted on said support and coaxial with said laser for rotation therewith, said detector having an aperture for passing said light beam.

11. The method of inspecting the surface of a part to define a plot, over the area of the part, of relative intensities of light reflected from the part surface, said method comprising projecting a light beam in a circular scan pattern of parallel paths perpendicular to a given plane, moving the part across the beam paths to cause the beam to impinge upon and be reflected from a plurality of successive points on the surface of said part, detecting light reflected from the surface of said part back along the paths of projected light, generating beam position signals representing positions of said light beam along its circular scan path at successive ones of a series of clock periods, generating scan pattern position signals representing relative positions of said part and said scan pattern at each of said clock periods, generating intensity signals having magnitudes directly related to intensities of detected light reflected from said part surface at each of said clock periods, whereby said signals collectively define a plot of intensity of light reflected from the part surface over the area of the part.

12. The method of claim 11 wherein said step of projecting a light beam in circular scan pattern comprises mounting a laser upon a rotating support, rotating the support adjacent the part to be inspected in a plane parallel to said given plane, mounting a detector on said support for rotation therewith, and employing said detector to receive light reflected from the part surface and to generate said intensity signals.

* * * * *